US011160778B2

(12) United States Patent
Rodriguez Vilaboa

(10) Patent No.: US 11,160,778 B2
(45) Date of Patent: Nov. 2, 2021

(54) COMPOSITION FOR USE IN THE PREVENTION AND/OR TREATMENT OF ONCOLOGIC TREATMENT INDUCED OROGASTROINTESTINAL MUCOSITIS

(71) Applicant: Mucosa Innovations, S.L., Madrid (ES)

(72) Inventor: Deborah Rodriguez Vilaboa, Madrid (ES)

(73) Assignee: MUCOSA INNOVATIONS, S.L., Madrid (ES)

( * ) Notice: Subject to any disclaimer, the term of this patent is extended or adjusted under 35 U.S.C. 154(b) by 0 days.

(21) Appl. No.: 16/635,458

(22) PCT Filed: Jul. 30, 2018

(86) PCT No.: PCT/EP2018/070594
§ 371 (c)(1),
(2) Date: Jan. 30, 2020

(87) PCT Pub. No.: WO2019/025366
PCT Pub. Date: Feb. 7, 2019

(65) Prior Publication Data
US 2020/0170988 A1  Jun. 4, 2020

(30) Foreign Application Priority Data

Jul. 31, 2017 (EP) .................................. 17382520

(51) Int. Cl.
| | |
|---|---|
| *A61K 36/00* | (2006.01) |
| *A61K 31/205* | (2006.01) |
| *A61P 1/00* | (2006.01) |
| *A61K 31/047* | (2006.01) |
| *A61K 36/63* | (2006.01) |
| *A61K 9/00* | (2006.01) |

(52) U.S. Cl.
CPC .......... *A61K 31/205* (2013.01); *A61K 31/047* (2013.01); *A61K 36/63* (2013.01); *A61P 1/00* (2018.01); *A61K 9/0053* (2013.01)

(58) Field of Classification Search
CPC ..................................................... A61K 36/00
USPC ....................................................... 424/725
See application file for complete search history.

(56) References Cited

FOREIGN PATENT DOCUMENTS

| | | |
|---|---|---|
| CN | 102526095 A | 7/2012 |
| EP | 2119477 A1 | 11/2009 |
| WO | WO 98/29090 | 7/1998 |
| WO | WO 2019/025366 A1 | 2/2019 |

OTHER PUBLICATIONS

Martin et al., "Products based on olive oil, betaine, and xylitol in the post-radiotherapy xerostomia," (2016) 22:1 71-76.
Abdulrhman et al., "Honey and a Mixture of Honey, Beeswax, and Olive Oil-Propolis Extract in Treatment of Chemotherapy-Induced Oral Mucositis: A Randomized Controlled Pilot Study," (2012) 29:3 285-292.
Muhamed Ahmed et al., "The effect of olive leaf extract in decreasing the expression of two pro-inflammatory cytokines in patients receiving chemotherapy for cancer. A randomized clinical trial," (2012) 25 141-147.
Chaveli-Lopez et al., "Treatment of oral mucositis due to chemotherapy," (2016) 8:2 e201-e2019.
Al-Ansari et al., "Oral Mucositis Induced By Anticancer Therapies," (2015) 2:4 202-211.
Int'l Search Report and Written Opinion of PCT/EP2018/070594 dated Oct. 2, 2018 (10 pages).
SYLOID 244 via Prospector, retrieved on Jan. 31, 2020 from https://wwww.ulprospector.com/es/eu/Food/Detail/985/107456/SYLOID-244 (1 page).
Thissen et al., "A systematic review of treatment modalities for primary basal cell carcinomas," (1999) 135:10 1177-1183.
ZEODENT 165—A true classic via Zeodent—Evonik Resource Efficiency GmbH (2020) 1-2.
Lalla et al., "MASCC/ISOO Clinical Practice Guidelines for the Management of Mucositis Secondary to Cancer Therapy," (2014) 1453-1461.
ZEODENT 163—Our product partner via Zeodent—Evonik Resource Efficiency GmbH (2020) 1-2.
World Health Organization, "WHO handbook for reporting results of cancer treatment," Publication No. 48 (1979) 1-46.

*Primary Examiner* — Michael V Meller
(74) *Attorney, Agent, or Firm* — Casimir Jones, S.C.

(57) ABSTRACT

The present invention refers to a composition for use in the prevention and/or treatment of orogastrointestinal mucositis induced by oncologic treatments. It also refers to the use of said composition for preparing a medicament for the prevention and/or treatment of said orogastrointestinal mucositis. Furthermore, it refers to a method of preventing and/or treating of said orogastrointestinal mucositis in which said composition is administered to a subject in need thereof.

8 Claims, No Drawings

COMPOSITION FOR USE IN THE PREVENTION AND/OR TREATMENT OF ONCOLOGIC TREATMENT INDUCED OROGASTROINTESTINAL MUCOSITIS

FIELD OF THE INVENTION

The present invention refers to the field of cancer therapy and its secondary effects, in particular it refers to a composition for use in the prevention and/or treatment of Oncologic Treatment Induced Orogastrointestinal Mucositis.

BACKGROUND OF THE INVENTION

Oncologic Treatment Induced Orogastrointestinal Mucositis is a cancer therapy-toxicity related mucosal injury of the alimentary tract that is recognized as a serious and debilitating side effect of cancer therapy. The mucosa of the respiratory tract is also a target for this toxicity. Thus, in the present invention, Oncologic Treatment Induced Orogastrointestinal Mucositis (abbreviated and referred to as OTIOM) is a mucosal injury of the aerodigestive tract, which comprises the alimentary tract and the respiratory tract, induced by cancer therapy.

Synonymous of OTIOM are "Orogastrointestinal Oncologic Mucositis", "Oncologic Mucositis", "Gastrointestinal Mucositis", also historically called "Oral Mucositis", abbreviated by some authors to "Mucositis", the latter leading to confusion with the non-malignant, non-life threatening local saliva-impairment related stomatitis or mucositis (see below).

OTIOM is currently the single most severe and more feared complication of cancer therapy. It often leads to unplanned treatment interruptions and chemotherapy dose reductions which reduce the loco-regional tumor control while allowing tumor repopulation which may lead to re-growth of chemotherapy-resistant cell population. Its morbidity is no longer underestimated leading to potentially a decrease in cancer survival rate, sepsis, and even fatal outcome during the cancer treatment.

All the ducts, cavities and organs that form the aerodigestive tract share a common feature, the mucosa barrier. OTIOM is primarily characterized by damage of not only the epithelium, as was historically thought, but the totality of the mucosa and the subjacent connective tissue.

OTIOM typically courses with mouth ulcers, pain that can make nutrition intolerable, vomiting, diarrhea, rectal bleeding and abdominal cramps, to name a few. It is autolimitating, but upon appearance leaves the patient prone to more episodes. Even though it preferably appears in the alimentary tract, proctitis following radiation is also considered a manifestation of OTIOM. Mucosal injury related to cancer therapy can occur in other mucosal barriers throughout the body, like vagina and even bronchi and lungs between others.

The incidence of OTIOM reaches 51% of all chemotherapy for solid tumors or lymphoma. In patients with high dosage chemotherapy before stem cell or hematopoietic cell transplantation this percentage rises to 75-80%. Patients treated for head and neck cancer develop OTIOM almost in 100% of cases, 29-66% of them in the severe form. In patients with radiotherapy for oral cancer, OTIOM will appear in 90-100% of the cases.

OTIOM is therefore a serious complication characterized by the onset of a disruption or breakage of the aerodigestive mucosa. At the initial stage it can happen as erythema or redness of the mucosa, with pseudomembranous lesions more or less extended that gradually merge until the mucosa is ulcerated throughout its depth. At this stage profuse bleeding with significant pain impair normal digestive tract function.

At the initial stages OTIOM usually appears as lesions in the mucosa of the oral cavity, classically originating the diagnosis of oral mucositis. The same type of lesions can simultaneously occur along the whole digestive tract. However, difficulty in diagnosis of the initial lesions of the mucosa in the internal organs of the digestive tract is delayed until more severe breakage of the mucosa barrier progresses to intolerable diarrhea with even visible bleeding through the anus.

In 1969, oral involvement of one of the most common diseases of the intestine, that is Crohn's disease, was described. More recently, Dupuy et al (Oral Crohn disease: clinical characteristics and long-term follow-up of 9 cases. Arch Dermatol 1999; 135:439-442) explained that many diseases of the digestive tract were easier to diagnose in the oral cavity that in the intestine because it is easily examined directly. In the same manner, Oral Mucositis is the expression in the oral cavity of OTIOM while Gastrointestinal Mucositis in the digestive tract, but both are the same clinical conditions.

One of the biggest difficulties regarding OTIOM resides in being able to describe precisely, objectively and in a reproducible way the severity of mucosal damage. Unfortunately regardless of a number of assessment scales available today there is still need for the definitive scale accepted universally for producing systematic validated data.

In the original publication from World Health Organisation (*WHO, Handbook For Reporting Results Of Cancer Treatment*. Geneva: WHO Offset Publication, 1979) a recommendation for grading the toxic effects of cancer therapy is found. WHO puts together a wide variety of signs and symptoms and grades them from 0 to 4 (see Table 1 of WHO Offset Publication 1979, of which the gastrointestinal part is extracted in Table 1 below).

TABLE 1

Recommendations for grading of acute and subacute toxic effects - Gastrointestinal

| | 0 | 1 | 2 | 3 | 4 |
|---|---|---|---|---|---|
| Bilirubin | ≤1.25 × $N^a$ | 1.26-2.5 × $N^a$ | 2.6-5 × $N^a$ | 5.1-10 × $N^a$ | >10 × $N^a$ |
| Transaminases (SGOT/SGPT) | ≤1.25 × $N^a$ | 1.26-2.5 × $N^a$ | 2.6-5 × $N^a$ | 5.1-10 × $N^a$ | >10 × $N^a$ |
| Alkaline phosphatase | ≤1.25 × $N^a$ | 1.26-2.5 × $N^a$ | 2.6-5 × $N^a$ | 5.1-10 × $N^a$ | >10 × $N^a$ |
| Oral | No change | Soreness/ erythema | Erythema, ulcers; can eat solids | Ulcers; requires liquid diet only | Alimentation not possible |

TABLE 1-continued

Recommendations for grading of acute and subacute toxic effects - Gastrointestinal

| | 0 | 1 | 2 | 3 | 4 |
|---|---|---|---|---|---|
| Nausea/Vomiting | None | Nausea | Transient vomiting | Vomiting requiring therapy | Intractable vomiting |
| Diarrhoea | None | Transient, < 2 d | Tolerable, but > 2 d | Intolerable, requires therapy | Haemorrhagic dehydration |

$N^a$ = upper limit of normal value of population under study.

This publication has inspired many others and one example is seen in Table 2, which outlines the main two of the multiple orogastrointestinal events that unfortunately may happen in a subject affected by OTIOM: Oral mucositis and diarrhea.

TABLE 2

WHO grading scale of oral mucositis and diarrhea (Koning et al, 2007, Chemotherapy Does Not Influence Intestinal Amino Acid Uptake in Children. Pediatric Research 62; 1995-199).

| Grade | Oral mucositis | Diarrhea |
|---|---|---|
| 0 | None | None |
| 1 | Oral soreness, erythema and pain | Transient, <2 d |
| 2 | Oral erythema, ulcers, can eat solids | Tolerable, but >2 d |
| 3 | Oral ulcers, requires liquid diet only | Intolerable, requires therapy |
| 4 | Oral alimentation not possible, nutrition by tube or total parenteral mandatory | Haemorrhagic dehydration |

Grades 3 and 4 are considered to be severe oral mucositis, and in the context of the present invention, are also considered as severe OTIOM.

More recently, regarding the relation of the origin of the toxicity on the severity of the presentation of the OTIOM it is usually accepted that radiotherapy with concomitant chemotherapy augments the severity of the lesions. New fractioned radiotherapy may have better local control but with more acute severe oral mucositis (rapid onset of the lesions). More recently, conformational radiotherapy with IMRT seems to reduce the risk of acute oral mucositis grade 3. Nonetheless all attempts to avoid presentation of OTIOM seem to be unsuccessful up until today.

Severe forms of OTIOM can require hospitalization, need for narcotic analgesics, can lead to suboptimal delivery of antineoplastic treatments, parenteral nutrition and are related with morbidity and mortality from sepsis, dehydration or other complications.

Current management of OTIOM is still managed only symptomatically, mostly by oncologists and onco-nurses. Most of the cases are seen in hospitals and require many times hospitalization. These patients are not seen neither followed by the dentist, whom instead does see moisture-deprived stomatitis or mucositis in cases of hyposalivation.

The management of OTIOM consists primarily in elimination or reduction of pain. Providing nutritional support through prevention of dehydration or providing rehydratation and prevention of malnutrition together with oral hygiene measures whenever possible and prevention of infections and/or sepsis, and handling digestive tract bleeding are the most important approaches during the acute episode. Lalla et al. (2014, MASCC/ISOO clinical practice guidelines for the management of mucositis secondary to cancer therapy. Cancer, 120 (10), 1453-1461) describe the clinical practice guidelines for the management of OTIOM (referred therein as mucositis secondary to cancer therapy). Said guidelines describe drugs such as lidocaine, fentanile, opiods and morphine that are used to control pain; do not recommend the use of chlorhexidine mouthwashes for the treatment of OTIOM, especially in the presence of ulceration; and do not recommend the use of antibiotics or acyclovir to prevent OTIOM on a routinely basis.

Apart from the symptomatic control described above, there is no clear therapeutic agreement, given the lack of clinical evidence in the literature, supporting any successful approach to either prevent or treat OTIOM.

Therefore, there is still a need in the state of the art of providing compositions for use in the prevention and/or treatment of OTIOM. Surprisingly, the authors of the present invention have developed a composition for such use.

OBJECT OF THE INVENTION

A first aspect of the present invention refers to a composition comprising olive oil, trimethylglycine and xylitol for use in the prevention and/or treatment of OTIOM.

A second aspect of the present invention refers to the use of a composition comprising olive oil, trimethylglycine and xylitol for the preparation of a medicament for the prevention and/or treatment of OTIOM.

A third aspect of the present invention refers to a method of treating OTIOM in a subject in need thereof, comprising administering to the subject a therapeutically effective amount of a composition comprising olive oil, trimethylglycine and xylitol.

A fourth aspect of the present invention refers to a method of preventing OTIOM in a subject which comprises administering to the subject a prophylactically effective amount of a composition comprising olive oil, trimethylglycine and xylitol.

A fifth aspect of the present invention refers to a composition comprising:
olive oil,
trimethylglycine,
xylitol, and
hydroxytyrosol and/or tyrosol and/or oleuropein.

Other objects, features, advantages and aspects of the present application will become apparent to those skilled in the art from the following description and appended claims.

BRIEF DESCRIPTION OF THE FIGURES

FIG. 1 shows the design of the study carried out in Example 5 (Study of treatment of proctitis). Subjects were separated into two groups, Group I and Group II. Group I received composition A on week 1 and composition B on week 3. Group II received composition B on week 1 and composition A on week 3. None of the groups received any treatment on week 2 (washout).

FIG. 2 shows the design of the study carried out in Example 6 (Comparative study of treatment of proctitis). Subjects were separated into two groups, Group I and Group II. Group I received composition A on week 1 and composition B on week 3. Group II received composition B on week 1 and composition A on week 3. None of the groups received any treatment on week 2 (washout).

DETAILED DESCRIPTION OF THE INVENTION

As used herein, the singular forms "a," "an" and "the" include their corresponding plural forms unless the context clearly indicates otherwise. Unless defined otherwise, all the technical and scientific terms used herein have the same meaning as commonly understood by a person skilled in the art to which this invention belongs. To facilitate understanding and clarify the meaning of specific terms in the context of the present invention, the following definitions and particular and preferred embodiments thereof, applicable to all the embodiments of the different aspects of the present invention, are provided:

OTIOM refers to orogastrointestinal mucositis induced by a cancer therapy. As explained above, OTIOM is a mucosal injury of the aerodigestive tract, which comprises the alimentary tract and the respiratory tract, induced by cancer therapy. Thus, in a particular embodiment, OTIOM affects the alimentary tract and/or respiratory tract. In another particular embodiment, OTIOM affects one or more parts selected from the group consisting of oral cavity, tongue, lips, pharynx, esophagus, stomach, intestine, rectum, anus, nose, nasal tract, paranasal sinuses, throat, vocal cords, and larynx. More particularly, OTIOM affects the oral cavity, lips, tongue, esophagus, stomach, intestine, rectum, anus and combinations therefore, more preferably, the oral cavity. In another particular embodiment, the oncologic treatment that induces orogastrointestinal mucositis is selected from the group consisting of chemotherapy, radiotherapy, immunotherapy, hormonal therapy, stem cell transplantation and combinations thereof. These terms are well known by the skilled in the art. Preferably, the oncologic treatment is chemotherapy and/or radiotherapy.

As mentioned in the background section, some authors classified OTIOM grades according to WHO's recommendations for grading of acute and subacute toxic effects of cancer therapy. Konrad classified the grades of the main affections of OTIOM: oral mucositis and diarrhea (see Table 2, above). Thus, in the present invention, the grading shown in Table 2 is considered to be the grading of OTIOM, and grades 3 and 4 are considered as severe OTIOM.

OTIOM should not be confused with the so called periimplantitis or peri-implant mucositis commonly discussed in the field of implant dentistry, a chronic affection of the support bone surrounding dental implants that has in the loss of the implant the most notorious consequence and that is often asymptomatic.

Likewise, OTIOM should not be confused with dysphagia and xerostomia, which happen in the oral environment. A number of conditions might be the origin of dysphagia and xerostomia in patients with cancer. Surgery and radiation of the head and neck are a clear cause for these two chronic oral complications, but neurological disorders, age, degenerative conditions, Sjögren syndrome, diabetes, and polymedication between others are also common diagnoses that explain these two symptoms and do not necessarily imply that the patient has cancer.

Dysphagia is a debilitating, depressing, and potentially life-threatening complication in cancer patients that is likely underreported and described as a swallowing disturbance due essentially to muscular conditions. Dysphagia is related to a number of factors such as direct impact of the tumor, cancer resection, chemotherapy, and radiotherapy and to newer therapies such as epidermal growth factor receptor inhibitors.

Xerostomia, also called dry mouth syndrome and burning mouth, is diagnosed when the amount or quality of saliva diminishes (hyposalivation). The prevalence of xerostomia is 22-26% in the general population, and 50-55% in mixed oncology populations. It has an origin in an alteration of the salivary gland normal function with a change in the histology of the gland parenchyma and acini. The etiology is usually polypharmacy or intake of mouth-drying drugs. Furthermore in head and neck cancer patients, xerostomia is a highly common complication of radiotherapy due to the irreversible damage to the salivary glands, remaining as a chronic collateral effect in a 93% of this group of patients. Surgery can also originate dry mouth syndrome. Thus, xerostomia is one of the most common complications experienced by all groups of oncology patients. However, perception of this somewhat chronical, low profile syndrome, is unimportant for many oncotherapists and patients, viewing other symptoms more important. Xerostomia affects significantly quality of life but is never a challenge for the patient survival. Many patients tolerate a diminished or poor salivary function and learn to live with it. In fact, 50% of xerostomia patients do not show any symptoms, and what is scientifically more relevant up to 50% of salivary flow may be lost before xerostomia manifests itself with signs or symptoms without yet perceiving dryness in the mouth.

Xerostomia can cause many chronic faringitis and a cohort of signs and symptoms labeled as stomatitis or mucositis (unspecific stomatitis-mucositis), the latter a non-malignant, non-life threatening local saliva-impairment manifestation of lack of moisture with a cohort of signs and symptoms like tongue fissures, dysgeusia (lack or altered taste), oral soreness, inability to wear dentures, affecting purely the mouth generally with a chronic course. Oral mucosa appears intact with a dull or anodyne redness, flatness or smoothness of the oral mucosa and tongue or in the contrary with increased rugosities and villis from the tongue also named "glositis", with or without white furry tongue.

Due to the sustained lack of lubricant, roughness causes oral irritation, especially in locations in contact with poorly fitting, inadequate or aged prosthesis. In this situation a candidiasis or infection by candida may superimpose. This so called candida mucositis or candida stomatitis is successfully treated with antifungical drugs and is in most cases asymptomatic.

All these clinical scenarios of unspecific stomatitis-mucositis are local, non-malignant, and never a challenge to the patient's life. They are diagnosed and treated by the dentist at the dental office through stimulating the salivary flow and/or polishing existing worn-out roughened restorations or via delivery of new prosthesis or restorations with highly polished materials and adequate designs.

Xerostomia and this xerostomia related stomatitis-mucositis, have generally a chronic course, and no matter how persistent they are, they will not lead to the onset of OTIOM, nor to diarrhea, nor vomits, nor anal bleeding nor ulceration of the alimentary canal neither the airway. They do not require hospitalization, or parenteral nutrition, or intravenous opioids, or advanced medical support, or in any case are they related to mortality.

"Prevention" refers to the absence of severe OTIOM, i.e. absence of OTIOM in the grades of 3 and 4. Thus, with the prevention of the present invention the subject will not have oral ulcers which make him require liquid diet only or impede oral alimentation completely (i.e. forces nutrition by tube or parenteral nutrition only). Moreover, the subject will not have intolerable diarrhea that requires therapy or rehydration. Moreover, the prevention refers to a reduction of the appearance of mild and moderate OTIOM (grades 1 and 2, or grade 2), compared to subjects not using the composition of the invention (see Example 1).

"Prophylactically effective amount" refers to an amount that is effective to eliminate the symptoms of severe OTIOM.

"Treatment" refers to the reduction of the symptoms and/or reduction of the duration of the symptoms of all grades of OTIOM. Preferably, it refers to the reduction of the symptoms and of the duration time of OTIOM.

"Therapeutically effective amount" refers to an amount that is effective to reduce the symptoms and/or duration of the symptoms of all grades of OTIOM.

In a first aspect, the present invention refers to a composition comprising olive oil, trimethylglycine (TMG) and xylitol (hereinafter referred to as composition of the invention) for use in the prevention and/or treatment of OTIOM.

Compositions comprising olive oil, TMG and xylitol are already known in the state of the art, see for example U.S. Pat. No. 8,540,970 B2. In particular, U.S. Pat. No. 8,540,970's composition can be used for the treatment of xerostomia. However, as mentioned above, xerostomia and xerostomia-induced stomatitis-mucositis are conditions completely different to OTIOM, and xerostomia does not lead to the onset of OTIOM. Moreover, the risk factors for the development of OTIOM may be categorized as tumor-related, treatment-related, and patient-related, among them a possible genetic predisposition. Xerostomia does not appear in any of these categories (Epstein et al., 2012, Cancer, "Oral Complications of Cancer and Cancer Therapy").

Furthermore, nothing in the state of the art suggests that a proper salivary function would prevent OTIOM from occurring, nor that patients with a maintained salivary flow would be OTIOM-risk free. In fact, patients with OTIOM do not tolerate any stimuli in the mouth and the use of saliva stimulants with its best representative, pilocarpine, has shown no beneficial effect in preventing or treating OTIOM (Lalla, et al., 2014).

Thus, an expert in the field, in view of the general malaise of these patients, especially with OTIOM of grade 3 or 4, and the overall intolerance not only to solids but also to liquids (to the point that they have to remove saliva from their mouths with a gauze in order not to swallow), would have been motivated not to recommend salivary stimulation for this type of patients.

Thus, even when compositions comprising olive oil, TMG and xylitol have already been described, in particular for use in the treatment of xerostomia, the skilled in the art would not have been motivated to use such composition for the prevention and/or treatment of OTIOM.

In relation to the different components of the composition of the invention, none of them has been individually linked with the prevention and/or treatment of OTIOM as defined in the present invention. Olive oil is the main ingredient of the well documented and internationally respected Mediterranean diet. Would olive oil "per se" be effective to prevent OTIOM, given the widespread and significant intake of olive oil in Mediterranean countries, the prevalence of OTIOM would be less common or non-existing in this geographical area. However, this is not the case, even when fairly conclusively data have demonstrated that people that live in the Mediterranean countries and follow the Mediterranean diet enjoy health benefits, namely in cardiovascular, degenerative but also enjoy cancer benefits especially lower breast and colon cancer figures.

Moreover, it has been shown that in oral mucositis grade 3 there were no significant differences between the use of honey alone or the use of honey mixed with the olive oil-propolis extract and beeswax, while in mucositis grade 2 the efficacy in reducing recovery time proven for honey alone, was reduced when honey was mixed with the olive oil-propolis extract and beeswax (Abdulrhman et al., *Pediatric Hematology and Oncology* (2012) 29, 285-292, "Honey and a Mixture of Honey, Beeswax, and Olive Oil—Propolis Extract in Treatment of Chemotherapy-Induced Oral Mucositis: A Randomized Controlled Pilot Study"). Thus, olive oil does not seem to be beneficial in the treatment of chemotherapy-induced oral mucositis.

Xylitol, has proven to be effective fighting caries as it is non fermentable by most oral bacteria. It has also been proved that it does not change the digestive microflora. No evidence supports the relation of xylitol with the immediate wellbeing and relief that patients with OTIOM obtain with the administration of the composition of the present invention.

TMG has been related in the U.S. Pat. No. 6,156,293 with the improvement of skin and skull dryness, but not with improvement of cancer therapy related mucosal injury or of ulceration of the orogastrointestinal mucosa.

Surprisingly, the composition of the present invention, comprising olive oil, TMG and xylitol, is useful for the prevention and/or treatment of OTIOM.

TMG has osmoprotective action and has no surfactant action. It should not be confused with the cocamidopropyl betaine (CAPB), being this one a detergent with surfactant action commonly used in oral hygiene products. In the composition of the present invention all detergents are excluded, specially taking into consideration that the group of patients encompasses a challenge to the mucosal integrity and detergents are totally deleterious in such case. Thus, in a particular embodiment, the composition of the present invention, according to any one of the embodiment of the present invention, does not comprise any detergent. Thus, the composition of the invention does not comprise sodium lauryl sulphate, sodium lauryl sarcosinate, CAPB, or detergents commonly used in oral hygiene products, preferably it does not comprise sodium lauryl sulphate, sodium lauryl sarcosinate or CAPB. Likewise, in a preferred embodiment according to any one, of the previous embodiments, the composition of the invention does not comprise alcohol, since alcohol may dry out the mouth and increase pain.

In a particular embodiment according to any one of the previous embodiments, the composition of the invention comprises 0.1%-5% by weight of olive oil, preferably 0.2%-4% by weight of olive oil, and more preferably 0.2%-2.5% by weight of olive oil. As shown in the Examples, compositions comprising an amount of olive oil within these ranges are very effective in the prevention and treatment of OTIOM.

All the percentages given in the present invention, are given in weight by weight of the total composition (w/w), unless otherwise stated.

In a particular embodiment according to any one of the previous embodiments, the composition of the invention comprises 0.1%-10% by weight of TMG, preferably 1.5%-6% and more preferably 2%-4% by weight.

In a particular embodiment according to any one of the previous embodiments, the composition of the invention comprises 1%-50% by weight of xylitol, preferably 1%-30% and more preferably 1-15%, and even more preferably 10%.

In a preferred embodiment, the composition of the invention comprises 0.2%-4% by weight of olive oil, 1.5%-6% by weight of TMG and 1%-30% by weight of xylitol.

In another preferred embodiment, the composition of the invention comprises 0.2%-2.5% by weight of olive oil, 2%-4% by weight of TMG and 1%-15% by weight of xylitol.

As shown in the Examples, compositions comprising an amount of olive oil, TMG and xylitol within the ranges defined above are very effective in the prevention and treatment of OTIOM.

In another preferred embodiment, the composition of the invention comprises olive oil, TMG and xylitol in the amounts defined in any one of the formulations described in the Examples (formulations 1-6).

In a particular embodiment according to any one of the previous embodiments, olive oil is extra virgin olive oil. In another particular embodiment, the composition does not comprise any other vegetable oil, except essential oils. Like this, the use of oils of lower quality, e.g. palma oil, is avoided, since the use of these oils has been recently linked with highly significant increase and size of the metastasis of human oral carcinoma.

In a particular embodiment according to any one of the preceding embodiments, the composition comprises an antioxidant, preferably a natural antioxidant. Particularly, the antioxidant is selected from the group of tocopherol acetate, vitamin C, hydroxytyrosol, tyrosol, oleuropein, and mixtures thereof.

Interestingly, hydroxytyrosol, tyrosol and oleuropein potentiate the anti-inflammatory, anti-bacterial and anti-oxidant activities of the olive oil, and appear to be able to stabilize the composition (i.e. reducing, or even eliminating, the need of further preservatives which will make the formulation more tolerable by the subjects, particularly if they suffer severe OTIOM). Thus, in a preferred embodiment the composition comprises hydroxytyrosol and/or tyrosol and/or oleuropein, preferably it comprises hydroxytyrosol, tyrosol and oleuropein. These three antioxidants can be provided using olive fruit extract.

Examples of composition comprising these antioxidants are the formulation 5 and 6 of the present invention, which are therefore preferred.

In another particular embodiment according to any one of the embodiments previously described, the composition does not comprise a source of fluorine. Like this, it can be swallowed, i.e. reaching other parts of the digestive tract apart from the oral cavity, without any contraindication for the subject. Examples of formulation not comprising fluorine sources are the formulation 5 and 6 of the present invention, which are therefore preferred, especially for the treatment of OTIOM, in particular OTIOM of grade 3 and 4

In another particular embodiment according to any one of the previous embodiments, the composition of the invention further comprises one or more components selected from the group consisting of remineralising agents, viscosity-controlling agents, moisturising agents, preservatives, colorants, pH-regulating agents, sweeteners, proteolytic enzymes, emulsifiers, abrasives, essential oils, cicatrizing agents, aromas, antioxidants, animal or plant gelatines, excipients, and a mixture thereof.

Preferably, the composition of the invention according to any one of the previous embodiments, comprises a cicatrizing, an antioxidant, a buffer, a preservative, a moisturizing and a solvent (preferably water); and optionally a rheological agent and/or an emulsifier. In a particular embodiment according to any one of the embodiments disclosed in the present paragraph, the composition comprises a sweetener, a colorant, an aroma, an essential oil, an abrasive, a proteolytic enzyme, a remineralising or combinations thereof.

In another preferred embodiment according to any of the preceding embodiments, the composition of the invention does not comprise either aroma or essential oil. This embodiment is specially preferred in cases of treatment of OTIOM, preferably severe OTIOM, to facilitate tolerance by the patient.

In another preferred embodiment according to any of the preceding embodiments, the composition of the invention does not comprise either of abrasive agent, fluorine source or proteolytic enzyme. This embodiment is specially preferred in cases of treatment of OTIOM, preferably of severe OTIOM, to facilitate tolerance by the patient.

Thus, in a more preferred embodiment according to any of the preceding embodiments, the composition of the present invention does not comprise either of aroma, essential oil, abrasive agent, fluorine source or proteolytic enzyme. This composition is preferably used for the treatment of OTIOM, preferably of severe OTIOM.

These further components of the composition of the invention are commonly known by the skilled in the art, and non-limiting examples of said compounds are given below. In a particular embodiment according to any one of the preceding embodiments, these compounds are selected from the examples given below.

The remineralising agents provide ions that allow remineralisation, specifically fluorine from any appropriate source (fluorine source), calcium from any appropriate source, as well as phosphates or other ions with remineralising capacity and capable of hardening the teeth.

The remineralising agent can be selected from the group consisting of fluoride anions, phosphate anions, calcium cations, sodium cations, potassium cations and mixtures thereof. Among the aforementioned the following are cited as examples: potassium fluoride, sodium fluoride, sodium monofluorophosphate, tin fluoride, amine fluorides (hexadecylamine hydrofluoride, bis-(hydroxyethyl)aminopropyl-Nhydroxyethyl-octadecylamine dihydrofluoride, N—N',N'-tri (polyoxyethylene)-N-hexadecyl-propylenediamine dihydrofluoride or octadecenylamine hydrofluoride), potassium phosphate, potassium pyrophosphate, tripotassium citrate, calcium lactate, calcium pantothenate and calcium carbonate. Potassium fluoride, sodium fluoride, sodium monofluorophosphate, tin fluoride, amine fluorides are fluorine sources. Thus, in those embodiments in which the composition does not comprise fluorine source but comprise a remineralising agent, the remineralising agent will not be a fluorine source.

Any rheologic agent known in the state of the art can be used as viscosity-controlling agents. In particular, the rheologic agent can be selected from the group consisting of gum arabic, tragacanth gum, xanthan gum, carboxymethyl cellulose (CMC), carbopol-type polymers, pectins, mucines and mixtures thereof.

Any moisturising agent known in the state of the art can be used in the composition of the invention. In particular, the moisturising agent can be selected from the group consisting of glycerine, propylene glycol, sorbitol and mixtures thereof, preferably glycerine.

Among the preservatives that can be used in the composition of the invention, sodium benzoate, benzoic acid, potassium sorbate, diazolidinyl urea, imidazolinyl urea, sodium methylparaben, sodium propylparaben, and mixtures thereof are preferred.

Any colorant of the state of the art can be used in the composition of the invention. In particular, the colorant can be selected from the group consisting of C.I. 75810, titanium dioxide and mixtures thereof.

In the composition of the invention any pH-regulating agent (also referred to as buffer) known in the state of the art can be used. In particular, the pH-regulating agent can be selected from the group consisting of lactic acid, lactates, citric acid, citrates, malic acid and salts thereof, sodium hydroxide, potassium phosphates, sodium phosphates, potassium pyrophosphate, sodium pyrophosphates and mixtures thereof.

Any sweetener known in the state of the art can be used in the composition of the invention. In particular, the sweetener can be selected from the group consisting of maltitol, isomaltitol, mannitol, lactitol, sodium saccharine, acesulfame potassium, aspartame, cyclamate, taumatin, sucralose, estevia rebaudiana, neohesperidine DC and mixtures thereof. Proteolytic enzymes such as papain, for example, can also be incorporated to the composition of the invention. This can be useful when mucosal injury lesions are present since it facilitates cleaning of the debris and reduces the dead cells that have been accounted for spurring the disruption of the mucosa.

Any suitable emulsifier known in the art can be used in the composition of the invention. In particular, the emulsifier can be selected from the group consisting of polyethylene glycol (PEG) 40 hydrogenated castor oil, lecithin and mixtures thereof.

A mild abrasive agent can also be used in the composition of the invention, preferably low abrasion silica, in particular, selected from the group consisting of hydrated silicas (such as Syloid 244, Zeodent 163, Zeodent 623).

As mentioned above, the composition of the invention can incorporate essential oils such as parsley seed oil and/or *Citrus medica* oil.

Any cicatrizing agent known in the state of the art can be used in the composition of the invention, in particular, selected from the group consisting of allantoin, D-panthenol, calcium pantothenate, and mixtures thereof.

The composition of the invention can comprise animal and/or plant gelatine such as bovine gelatine, fish gelatine, algae gelatine, and mixtures thereof.

The composition of the invention can also include aromas such as *Citrus medica* or mint extracts, for example.

Finally, suitable excipients will be added to the composition of the invention according to the formulation they are intended for. Thus, beeswax, gum base, carnauba wax or shellac, etc can be used.

In another particular embodiment according to any of the previous embodiments, the composition of the invention does not comprise any additional active principle. In particular, it does not comprise pilocarpine, pentoxifylline, cyclosporine, granulocyte-macrophage-colony-stimulating factor, anti-interleukin-6 antibody, acyclovir, antimicrobial agents, chlorhexidine, mesalazine, olsalazine, sucralfate, 5-acetyl salicylic acid, misoprostol, or combinations thereof. More particularly, it does not comprise honey and/or propolis. According to the desired presentation/formulation, the composition can include all those components necessary to provide the desired organoleptic and rheologic form.

Preferably, the composition of the invention has a neutral pH (between 6 and 7.5). Moreover, in the case of liquid and doughy preparations, water is used as a solvent. During the treatment of the OTIOM an aqueous solution is preferred and the need for an emulsifier is reduced. Thus, in a preferred embodiment according to any one of the embodiment of the first aspect of the invention, the composition is an aqueous solution and it does not comprise an emulsifier.

In a particular embodiment, the composition of the invention is formulated as solution (e.g. mouthwash), spray, gel, syrup, toothpaste, chewing gum, suckable capsules, suckable lozenges, palate sheets, tablets, sweets, impregnated oral swabs, impregnated oral gauzes, sucking tablets, topical solutions, topical ointments with or without applicators.

The solution, spray, gel and syrup are considered in the present invention as liquid dosage forms. In a preferred embodiment according to any one of the previous embodiments, the composition of the invention is formulated as an aqueous liquid dosage form.

In general, as well as the swabs and gauzes, any suitable support impregnated with a solution of the composition of the invention can be used for topical application in the mouth, throat, nose or anus. Likewise, a single dose presentation (a suitable sachet or blister, for example) of the composition of the invention can be used, which can optionally be cooled before use so a faster and more effective alleviation from the pain is achieved. Preferably, the liquid dosage form of the composition is ingested so that it acts on the mucosa of the whole alimentary tract.

In any case, the skilled in the art will formulate the composition of the invention in any suitable presentation that allows a simple use for the prevention and/or treatment of OTIOM. The composition of the invention has been proved to prevent OTIOM when used daily as soon as possible after the cancer is diagnosed and ideally at least 24 h before starting the oncologic treatment (see Example 1). This protocol should be continued along the whole duration of the cancer treatment. If the subject already has symptoms of OTIOM, in order to prevent developing to grades 3 and 4, the composition of the invention is preferably applied within the first 24 hours after onset or diagnosis of OTIOM.

The composition of the invention has been proved to treat OTIOM. The treatment composition should be used daily along the duration of the OTIOM episodes and at least two weeks after the cessation of signs and symptoms (see Example 2). If radiation of rectum or prostate is given, the composition of the invention is applied locally to the anus.

A preferred administration protocol for the treatment of OTIOM is to apply the composition of the invention, with or without an applicator, while gently opening the mouth and spreading it throughout the mucosa while swallowing the excess, so there is contact between the mucosa and the composition not only in the mouth but also throughout the whole alimentary tract. Preferably, the composition does not comprise any source of fluorine, this is specially preferred when the subject has severe OTIOM.

Preferably the dosage is 2.5 to 5 ml per application, equivalent to a tea spoon. Preferably, this is applied at least 3 times a day, more preferably at least 6 and even more preferably a maximum of 10 times a day. Thus, in a preferred embodiment, the composition is administered between 3 and 10 times per day.

In a preferred embodiment of the invention according to any one of the preceding embodiments, the composition is a liquid dosage form, preferably an aqueous liquid dosage form, and more preferably an aqueous solution or an aqueous gel. Like this, it can be easily applied in the affected areas and even swallowed.

In a particular embodiment of the invention according to any one of the embodiments of the first aspect of the invention, the administration protocol is the one described in Example 1 or in Example 2.

A second aspect of the present invention refers to the use of a composition comprising olive oil, trimethylglycine and xylitol for the preparation of a medicament for the prevention and/or treatment of OTIOM. The particular and preferred embodiments of the composition of the invention described for the first aspect of the invention are applicable to the second aspect of the invention.

A third aspect of the present invention refers to a method of treating OTIOM in a subject in need thereof, comprising administering to the subject a therapeutically effective amount of a composition comprising olive oil, TMG and xylitol. The particular and preferred embodiments of the composition of the invention described for the first aspect of the invention are applicable to the third aspect of the invention.

In a particular embodiment of the third aspect of the invention, the method of treating OTIOM in a subject in need thereof, comprises administering to the subject a therapeutically effective amount of the composition of the invention as defined in any of the embodiments of the first aspect of the invention, said administration to the subject being commenced as soon as the first signs and symptoms appear. It is given daily, at least 3 times a day, preferably at least 6 times. Preferably it is not administered more than 10 times per day. Thus, in a particular embodiment, the composition is administered between 3 and 10 times per day, preferably between 6 and 10 times per day. In a preferred embodiment according to any one of the preceding embodiments, the dosage is 2.5 to 5 ml per application, equivalent to a tea spoon. The composition is administered with or without an applicator, while gently opening the mouth and spreading it throughout the mucosa while swallowing the excess.

In a preferred embodiment according to any one of the preceding embodiments of the third aspect of the invention, the composition is formulated as a liquid dosage form, more preferably as an aqueous liquid dosage form and even more preferably as an aqueous solution. In a preferred embodiment according to any one of the preceding embodiments, the composition does not comprise any fluorine source. More preferably it comprises hydroxytyrosol, tyrosol and oleuropein. And even more preferably, the composition is the one of formulation 5 or 6.

In a preferred embodiment, the protocol of administration of the composition of the invention is as described in Example 2.

Preferably, the administration of the composition of the invention is administered along the whole duration of the cancer treatment, and more preferably during at least two weeks more after the end of the cancer treatment.

A fourth aspect of the present invention refers to a method of preventing OTIOM in a subject which comprises administering to the subject a prophylactically effective amount of a composition comprising olive oil, TMG and xylitol. Said administration to the subject being commenced as soon as possible after being diagnosed with cancer and knowing when the cancer-therapy starts, and at least 24 hours before starting the oncologic treatment. The composition should be administered during the whole cancer treatment, preferably without stopping between therapy cycles. If the subject already has symptoms of OTIOM, in order to prevent developing to grades 3 and 4, the composition of the invention is preferably applied within the first 24 hours after onset or diagnosis of OTIOM.

Preferably an aqueous liquid dosage form, more preferably an aqueous solution, is topically applied to the oral mucosa with topical application of 2.5-5 ml of the composition of the invention. It is applied daily, several times a day, starting at least 24 h before the cancer therapy regimen is started. In a preferred embodiment, the protocol of administration is as described in Example 1, without being limited to the formulation therein described.

A fifth aspect of the present invention refers to a composition comprising olive oil, TMG and xylitol, according to any one of the embodiments of the composition of the invention described in the first aspect of the invention. Particularly, it refers to a composition comprising an antioxidant selected from the group consisting of hydroxytyrosol, tyrosol, oleuropein and mixtures thereof (i.e. hydroxytyrosol and/or tyrosol and/or oleuropein). Preferably, it comprises hydroxytyrosol, tyrosol and oleuropein.

In another particular embodiment, the composition does not comprise a source of fluorine.

Examples, of composition comprising these antioxidants and without fluorine sources are the formulation 5 and 6 of the present invention, which are therefore preferred embodiments of the fifth aspect of the invention.

EXAMPLES

Specific embodiments of the invention that serve to illustrate the invention without limiting the scope thereof are described in detail below.

Example 1.—Study of Prevention of OTIOM 1.1.—Subjects

Fifty four patients (26 men and 28 women) aged from 12 to 95 with different cancer diagnosis (Table 3) and different oncologic treatments (surgery, chemo-radiotherapy, radiotherapy or a combination of them) (Table 4) were included in the study.

TABLE 3

| Cancer diagnose | Total cases | Test group | Control group |
|---|---|---|---|
| Head and neck | 14 | 7 | 7 |
| Colorectal | 4 | 1 | 3 |
| Stomach | 2 | 2 | 0 |
| Gastrointestinal carcinoid | 1 | 1 | 0 |
| Leukemia | 5 | 5 | 0 |
| Lymphoma | 4 | 3 | 1 |
| Breast | 10 | 7 | 3 |

TABLE 3-continued

| Cancer diagnose | Total cases | Test group | Control group |
|---|---|---|---|
| Melanoma | 1 | 1 | 0 |
| Pancreatic | 2 | 2 | 0 |
| Prostate | 3 | 2 | 1 |
| Lung | 8 | 7 | 1 |

TABLE 4

| Treatment | Number of patients |
|---|---|
| Surgery + Chemotherapy + Radiotherapy | 34 |
| Surgery + Chemotherapy | 7 |
| Chemotherapy | 10 |
| Surgery + Radiotherapy | 2 |
| Chemotherapy + Radiotherapy | 1 |

1.2.—Inclusion and Exclusion Criteria

Inclusion

Patients with a cancer diagnosed, who require an oncologic treatment as chemotherapy and/or radiotherapy with or without surgery. Patients with a good oral hygiene habit and with the intention of using the products following the protocol received.

Exclusion

Those patients who did not comply with the inclusion criteria were excluded of the study.

1.3.—Study Design

Thirty eight out of the 54 patients with a diagnosed cancer had not started with any of the oncologic treatments before the beginning of the study. These patients were asked to use the test products with the defended composition at least 24 h in advance to the oncologic treatment start up. This group of patients was namely the test group.

The other 16 patients did not use the products with the composition of the present invention. This group of patients was namely the control group.

The protocol consisted in:

Brushing teeth with the composition (formulation 1) after main meals.

Rinsing with the composition (formulation 2) before or after brushing (patient choice).

Applying the composition (formulation 3) or the composition (formulation 4) between brushings whenever the patient felt pain or discomfort.

Applying the composition (formulation 5) in the oral cavity with a small spoon at a dosage of 2.5 to 5 ml (equivalent to a tea spoon) before and after every chemo or radiotherapy session. Application by spreading the composition all around the oral mucosa with the tongue, lips or by means of mild mouth movements and swallowing the excess to allow the composition to act in the alimentary tract.

This protocol was continued during the whole duration of the cancer treatment. The test and control group reported at the end of the oncologic treatment the onset or not of OTIOM. Whenever OTIOM appeared, patient reported the degree diagnosed by his/her oncologist as per the WHO classification.

1.4.—Used Formulations

Formulation 1: Toothpaste

| Component | Percentage (w/w) |
|---|---|
| Olive oil | 2.225 |
| TMG | 4.000 |
| Xylitol | 10.000 |
| Others: cicatrizing (0.05%), abrasive (18%), antioxidant (0.05%), proteolytic enzyme (0.1%), remineralising (0.22%), buffer (3.2%), rheologic (1.2%), sweetener, preservative (0.1%), aroma (0.5%), essential oil (0.075%), colorant (1.0%), moisturizing (31.53%), water (27.75%). | 83.775 |

Formulation 2: Aqueous Solution (as Mouthwash)

| Component | Percentage (w/w) |
|---|---|
| Olive oil | 0.200 |
| TMG | 2.000 |
| Xylitol | 1.000 |
| Other agents: emulsifier (2%), cicatrizing (0.25%), antioxidant (0.05%), remineralising (0.07%), buffer (0.2%), preservative (0.65%), aroma (0.405%), essential oil (0.03), colorant (0.05%), moisturising (3%), water (90.095%). | 96.800 |

Formulation 3: Aqueous Gel

| Component | Percentage (w/w) |
|---|---|
| Olive oil | 1.111 |
| TMG | 4.000 |
| Xylitol | 10.000 |
| Other agents: cicatrizing (0.05%), antioxidant (0.05%), remineralising (1.0%), buffer (7.65%), rheological (2.5%), preservative (0.42%), essential oil (0.037%), aroma (0.5%), moisturizing (42.682%), water (30%). | 84.889 |

Formulation 4: Aqueous Spray

| Component | Percentage (w/w) |
|---|---|
| Olive oil | 1.000 |
| TMG | 2.000 |
| Xylitol | 10.000 |
| Other agents: emulsifier (5.75%), cicatrizing (0.7%), antioxidant (0.5%), remineralising (0.5%), buffer (0.2%), preservative (0.8%), aroma (0.405%), essential oil (0.143%), moisturising (3%), water (75.002%). | 87.000 |

Formulation 5: Aqueous Gel

| Component | Percentage (w/w) |
|---|---|
| Olive oil | 0.500 |
| TMG | 4.000 |
| Xylitol | 10.000 |

-continued

| Component | Percentage (w/w) |
|---|---|
| Other agents: rheological (1.1%), cicatrizing (0.05%), antioxidant (0.15%), pH regulating agent (2.5%), preservative (0.42%), moisturising (34.5%), water (46.78%). | 85.500 |

1.5.—Results

One out the 38 patients of the test group declared to not comply with the protocol due to personal reasons. Also one out the 16 patients of the control group declared to have interrupted the protocol. Both patients were excluded from the data analysis.

The results for the 37 patients of the test group were as follows (Table 5):

TABLE 5

| Grade 0 | Grade 1 | Grade 2 | Grade 3 | Grade 4 |
|---|---|---|---|---|
| 27 (72.97%) | 7 (18.92%) | 3 (8.11%) | 0 (0%) | 0 (0%) |

The results for the 15 patients of the control group were as follows (Table 6):

TABLE 6

| Grade 0 | Grade 1 | Grade 2 | Grade 3 | Grade 4 |
|---|---|---|---|---|
| 1 (6.67%) | 2 (13.33%) | 8 (53.33%) | 2 (13.33%) | 2 (13.33%) |

Differences in the number and grade of OTIOM reported from the control and test group were statistically significant ($p<0.0001$).

Differences in the number of patients that reported mild and moderate OTIOM (grades 1 and 2) from the test group versus the control group were statistically significant ($p<0.0409$). Said difference for OTIOM of grade 2 was also statistically significant ($p<0.01$).

Differences in the number of patients that reported severe OTIOM (grades 3 and 4) from the test group versus the control group were statistically significant ($p<0.0409$).

None of the studied patients developed gastrointestinal adverse effects as a result of swallowing of the composition of the invention. Also, no hypersensitivity reaction to treatment was observed in any patient.

1.6.—Conclusions

Using the compositions of the present invention prevents any OTIOM (i.e. OTIOM grade 0) in 73% of cases ($p<0.0001$).

Using the compositions of the present invention prevents severe and life-threatening OTIOM (Grades 3 and 4) in 100% of cases ($p<0.0409$).

Using the compositions of the present invention reduces the appearance of mild and moderate OTIOM (grades 1 and 2) ($p<0.0409$)

Example 2.—Study of Treatment of OTIOM 2.1.—Subjects

Twenty patients (8 men and 12 women) aged from 45 to 88 with different diagnosed cancers (Table 7) and different oncologic treatments (surgery, chemo-radiotherapy, radiotherapy or a combination of them) (Table 8) were included in the study.

TABLE 7

| Cancer diagnose | Number of patients |
|---|---|
| Head and neck | 9 |
| Colorectal | 3 |
| Lymphoma | 1 |
| Breast | 4 |
| Prostate | 1 |
| Lung | 1 |
| Esophagus | 1 |

TABLE 8

| Treatment | Number of patients |
|---|---|
| Surgery + Chemotherapy + Radiotherapy | 11 |
| Surgery + Chemotherapy | 2 |
| Chemotherapy | 5 |
| Surgery + Radiotherapy | 1 |
| Chemotherapy + Radiotherapy | 1 |

2.2.—Inclusion and Exclusion Criteria

Inclusion Criteria

Patients with diagnosed cancer, undergoing an oncologic treatment as chemotherapy and/or radiotherapy, with or without surgery, who having had developed mucositis in a previous cycle of treatment were noticing the onset of mucositis in a current cycle.

Oral hygiene measures were instructed by the oncological team, varying from normal oral hygiene measures to prohibition of tooth brushing.

Exclusion Criteria

Patients that were using the tested products before starting the study were not allowed to participate.

Those patients that did not comply with the inclusion criteria were excluded from the study.

2.3.—Study Design

Once the oncologic team detected orogastrointestinal mucositis, patient and nurse were instructed to use of the products following the protocol consisting in:

1. Before every chemo or radiotherapy session, applying 2.5 to 5 ml (equivalent to a tea spoon) of the composition (formulation 5) in the oral cavity with a small spoon. Spreading the solution all around the oral mucosa with the tongue, lips and mild mouth movements and swallowing the excess to allow the solution to act in the alimentary tract.
2. During the session days, applying the composition (formulation 5) whenever discomfort appears, or even in absence of discomfort applying the product at least 3 times per day.
3. Applying the composition (formulation 5) at least 3 times a day during non-session days.
4. Applying the composition (formulation 5) before going to bed. If patient wakes up during the night do another application.
5. Rinsing with the composition (formulation 6) after meals to remove excess debris and food remnants and spit.

This protocol should be followed during the whole cycle and kept for two more weeks after the cycle had ended and should be started as soon as the first signs and symptoms appear. A comparison of the duration of OTIOM between previous and current cycles was performed.

All patients were asked to fill in a short questionnaire regarding their prospective feelings of fear with which they faced the next treatment based on what they had experienced in the previous cycle. The answer was graded as 0 (no fear), 1 (moderate fear) and 2 (high fear). Patients were asked the same question before starting with the treatment and at the end of the two weeks posterior to the cycle of treatment end. Results were compared (see Table 11 below).

2.4.—Formulations

Formulation 5 (as Above):

| Component | Percentage (w/w) |
|---|---|
| Olive oil | 0.500 |
| TMG | 4.000 |
| Xylitol | 10.000 |
| Other agents: rheological (1.1%), cicatrizing (0.05%), antioxidant (0.15%), pH regulating agent (2.5%), preservative (0.42%), moisturising (34.5%), water (46.78%). | 85.500 |

Formulation 6: Aqueous Spray

| Component | Percentage (w/w) |
|---|---|
| Olive oil | 0.200 |
| TMG | 2.000 |
| Xylitol | 1.000 |
| Other agents: pH regulating agent (1%), emulsifier (2%), antioxidant (0.05%), preservative (0.65%), cicatrizing (0.05%), moisturising (2%), water (91.05%). | 96.800 |

2.5.—Results

One of the patients informed of non-compliance with the protocol for personal reasons, so he was excluded from the data analysis.

The rest of patients declared an immediate improvement because they experienced a reduction of the symptoms and a reduction in the duration time compared with OTIOM developed during previous cycles.

Due to the accumulative toxic effect described by many authors some patients were experiencing a higher grade of mucositis in the current cycle (before starting to use the composition of the invention) than in the previous cycle (see Table 9).

TABLE 9

| Comparison in the grade of mucositis between previous, before starting treatment with the composition, and current cycle | Number of patients |
|---|---|
| Same grade | 13 |
| One more grade | 5 |
| Two more grades | 1 |

Comparison in the duration time with OTIOM was done between the previous cycle (without administering the composition of the invention) and current cycle (administering the composition of the invention) only in those patients who developed the same grade of mucositis in both cycles.

Differences in the duration time by grade of OTIOM developed and as a whole between previous and current cycle are included in Table 10. Differences of all the grades are statistically significant (p=0.01).

TABLE 10

Average duration time with OTIOM by grades and as a whole between previous treatment cycle and current cycle.

| | Grade 4 | Grade 3 | Grade 2 | Grade 1 | Whole |
|---|---|---|---|---|---|
| Previous cycle (days) | 28 | 21 | 11 | 5 | 12.46 |
| Current cycle (days) | 16 | 8.5 | 4.5 | 1.33 | 5.27 |
| % reduction | 43 | 60 | 59.1 | 73.4 | 57.7 |

None of the studied patients developed gastrointestinal adverse effects as a result of swallowing of the composition of the invention. Also, no hypersensitivity reaction to treatment was observed in any patient.

All patients benefited from a significant reduction in the recovery time between the OTIOM episode treated with the composition of the invention, and previous episodes of OTIOM not treated with said composition.

Regarding the fear patients anticipated for the next treatment the authors of the invention included a simple question about how much fear they felt when they faced the next cycle of treatment, as explained in the last paragraph of section 2.3.

Fear is a major problem because an important number of patients drop the cancer treatment out of fear feeling incapable to endure the toxic effects of a new cycle. If the patients were less fearful probably they would be ready for the next treatment cycle and therefore fewer delays and fewer second line treatment options would be needed. The authors of the invention were satisfied with the results. As shown in Table 11, patients after using the composition of the invention felt more at ease with future treatments. Differences were statistically significant (p=0.05).

TABLE 11

| Average fear before current cycle with composition | Average fear after current cycle with composition |
|---|---|
| 0.75 | 0.5 |

After the completion of the study, the authors of the present invention found a better predisposition of the majority of the patients towards next treatment cycle, probably based on the fact that even in the cases whom had previously experienced nausea, mouth ulcers, vomiting, inability to eat or drink or even haemorrhagic diarrhea now felt that the composition of the invention would help them escape suffering any of these.

2.6.—Conclusions

The duration of OTIOM was reduced with the use of the composition of the present invention in all cases, i.e. when applied to patients with any grade of mucositis. The differences were statistically significant (p=0.01). All patients had a more confident attitude towards future treatment after using the composition of the present invention.

Example 3: Comparative Study of Prevention 3.1.—Subjects 60 patients (27 men and 33 women) aged from 25 to 78 with different cancer diagnosis and different oncologic treatments were included in the study.

3.2.—Inclusion and Exclusion Criteria

Inclusion

Patients with a cancer diagnosed, who require an oncological treatment which has not started yet. Patients intending to follow the protocol and having good oral hygiene.

Exclusion

Those patients who did not comply with the inclusion criteria. Moreover, patients that were using the tested products before starting the study were not allowed to participate.

3.3.—Study Design

Three randomized groups of 20 patients each were created.

Group 1: Composition comprising olive oil, TMG and xylitol.

Group 2: Composition comprising olive oil, but not including TMG nor xylitol.

Group 3: Composition comprising xylitol and TMG, but not including olive oil.

The protocol consisted of:

Brushing teeth with the assigned composition after meals.

Applying the assigned composition between brushings whenever the patient felt pain or discomfort.

Applying the assigned composition before and after every chemo or radiotherapy session.

This protocol was continued during the whole cancer treatment.

The three groups reported at the end of the oncological treatment the onset and the grade of OTIOM.

3.4.—Formulations

GROUP 1

| Component | Percentage (w/w) |
|---|---|
| Olive oil | 0.50 |
| TMG | 4.00 |
| Xylitol | 10.00 |
| Other agents: rheological (1.1%), cicatrizing (0.05%), antioxidant (0.15%), pH regulating agent (2.5%), preservative (0.42%), moisturising (34.5%), water (46.78%). | 85.50 |

GROUP 2

| Component | Percentage (w/w) |
|---|---|
| Olive oil | 0.50 |
| TMG | 0.00 |
| Xylitol | 0.00 |
| Other agents: rheological (1.1%), cicatrizing (0.05%), antioxidant (0.15%), pH regulating agent (2.5%), preservative (0.42%), moisturising (34.5%), water (60.78%). | 99.50 |

GROUP 3

| Component | Percentage (w/w) |
|---|---|
| Olive oil | 0.00 |
| TMG | 4.00 |
| Xylitol | 10.00 |
| Other agents: rheological (1.1%), cicatrizing (0.05%), antioxidant (0.15%), pH regulating agent (2.5%), preservative (0.42%), moisturising (34.5%), water (47.28%). | 86.00 |

3.5.—Results and Conclusions

The results of Groups 1, 2 and 3 are shown in Table 12.

TABLE 12

| Treatment | Grade 0 | Grade 1 | Grade 2 | Grade 3 | Grade 4 |
|---|---|---|---|---|---|
| GROUP 1 | 15 (75%) | 5 (25%) | 0 (0%) | 0 (0%) | 0 (0%) |
| GROUP 2 | 3 (15%) | 5 (25%) | 7 (35%) | 4 (20%) | 1 (5%) |
| GROUP 3 | 4 (20%) | 7 (35%) | 2 (10%) | 5 (25%) | 2 (10%) |

Group 1, using the composition of the invention (comprising olive oil, xylitol and TMG), did not develop OTIOM, measured as grade 0, in 75% of cases. In contrast, Group 2, using the composition with only olive oil, has 15% of patients with, grade 0, and Group 3, using the composition with xylitol and TMG, shows 20% of patients with grade 0. That is, only 15% and 20% of the patient of Groups 2 and 3, respectively, did not develop OTIOM. Furthermore, using the composition of the invention (Group 1) prevents severe and life-threatening OTIOM (grades 3 and 4) in 100% of cases, showing a statistically significant difference with the other two groups (p=0.01 with the Group 2, and p=0.03) with the Group 3). In contrast, in Groups 2 and 3, 25% and 35% of the cases, respectively, present severe and life-threatening OTIOM (grades 3 and 4).

Example 4: Comparative Study of Treatment 4.1.—Subjects

Sixty patients (37 women and 23 men) aged from 28 to 89 with different diagnosed cancers and different oncological treatments were included in the study.

4.2.—Inclusion and Exclusion Criteria

Inclusion

Patients with diagnosed cancer, undergoing an oncological treatment as chemo and/or radiotherapy, who developed mucositis in a previous cycle of treatment and were noticing the onset of mucositis in a current cycle.

Exclusion

Patients that were using the tested products before starting the study were not allowed to participate.

Patients that did not comply with the inclusion criteria were excluded from the study.

4.3.—Study Design

Three randomized groups of 20 patients each were created.

Group 1: Composition comprising olive oil, TMG and xylitol.

Group 2: Composition comprising olive oil, but not including TMG nor xylitol.

Group 3: Composition comprising xylitol and TMG, but not olive oil.

The protocol consisted of:

Brushing teeth with the assigned composition after meals.

Applying the assigned composition between brushings whenever the patient felt pain or discomfort.

Applying the assigned composition before and after every chemo or radiotherapy session.

This protocol was started as soon as the first signs and symptoms appeared and was followed during the whole cycle and kept for two more weeks after the cycle had ended. Comparison of the duration of OTIOM between previous and current cycles was performed.

4.4.—Formulations

GROUP 1

| Component | Percentage (w/w) |
|---|---|
| Olive oil | 0.50 |
| TMG | 4.00 |
| Xylitol | 10.00 |
| Other agents: rheological (1.1%), cicatrizing (0.05%), antioxidant (0.15%), pH regulating agent (2.5%), preservative (0.42%), moisturising (34.5%), water (46.78%). | 85.50 |

GROUP 2

| Component | Percentage (w/w) |
|---|---|
| Olive oil | 0.50 |
| TMG | 0.00 |
| Xylitol | 0.00 |
| Other agents: rheological (1.1%), cicatrizing (0.05%), antioxidant (0.15%), pH regulating agent (2.5%), preservative (0.42%), moisturising (34.5%), water (60.78%). | 99.50 |

GROUP 3

| Component | Percentage (w/w) |
|---|---|
| Olive oil | 0.00 |
| TMG | 4.00 |
| Xylitol | 10.00 |
| Other agents: rheological (1.1%), cicatrizing (0.05%), antioxidant (0.15%), pH regulating agent (2.5%), preservative (0.42%), moisturising (34.5%), water (47.28%). | 86.00 |

4.5.—Results

The effectiveness of the treatment can be measured by comparing the grade of mucositis of the current cycle with the grade of the previous cycle.

Due to the accumulative toxic effect, described by many authors, patients experience higher grade of mucositis in posterior cycles than in the previous cycles. Hence, a treatment success is when patients experience the same grade that in the previous cycle.

TABLE 13

| Comparison in the grade of mucositis between previous, before starting treatment with the composition, and current cycle | GROUP 1 | GROUP 2 | GROUP 3 |
|---|---|---|---|
| Same grade | 15 | 4 | 7 |
| One more grade | 5 | 13 | 10 |
| Two more grades | 0 | 3 | 3 |

As shown in Table 13, 75% of patients in Group 1 experienced the same grade of mucositis than in the previous cycle (i.e. successful treatment), while only 20% of Group 2 and 35% of Group 3 had the same grade than in the previous cycle.

Differences between Group 1 and Group 2 were statistically significant ($p<0.01$) as well as the differences between Group 1 and Group 3 ($p<0.01$). No differences were seen between Groups 2 and 3.

Example 5.—Study of Treatment of Proctitis 5.1.—Objective, Subjects and Formulations Proctitis, OTIOM affecting the rectum, is one late side effect of cancer treatment toxicity of the mucosa, not only in the rectum cancer patients, but most commonly in the prostate cancer being it the most frequent complication when radiotherapy is applied in high doses in the abdominal pelvic area. Radiation proctitis appears at any time after radiation of the pelvic area as a dose dependent toxic effect of the radiotherapy of cancer in the urological and gynecological or digestive apparatus and can affect 5-20% of this group of patients. Toxicity of rectal mucosa as a late side effect of chemotherapy has also been reported in the form of tenesmus and diarrhea followed by episodes of constipation.

Bleeding, in the most severe form of proctitis, may need ferrum intake and call in for differential diagnosis with cancer relapse or new cancerous disease.

While in the more aggressive presentation bleeding can lead to anemia and hence transfusions, it is generally receding after some time of clinical symptoms.

Diarrhea is accompanied with either mucous discharge or/and abdominal discomfort.

The objective of the study was to compare the clinical efficacy of a composition comprising xylitol, olive oil and TMG (i.e. composition according to the invention) with a placebo composition without any of the mentioned active ingredients in patients with proctitis after prostate cancer treatment.

To carry out the study, 20 patients were included in the study, and randomly divided into 2 groups. Two different compositions were tested:

Composition A (invention), comprising 0.5% Olive oil, 4.0% TMG and 10% Xylitol.

Composition B (placebo), comprising the same excipients that composition A, but with none of the active ingredients.

5.2.—Inclusion and Exclusion Criteria

Inclusion

Patients diagnosed with proctitis due to oncological treatment, and referring rectal discomfort/pain and rectal tenesmus were included in the study.

Exclusion

Those patients who did not comply with the inclusion criteria were excluded from the study.

5.3.—Study Design

The study was crossover so everyman used both compositions randomly assigned. Between the administration of one composition and the next one, there was one week of washout.

Products were packaged in white tubes identified with the number of patient. Content was kept in a closed envelope and only opened for data treatment.

Every complaint was assessed by a VAS (Visual analogue scale) 100 mm long.

VAS values reporting rectal discomfort/pain and rectal tenesmus were obtained for every patient at four different days:

Day 0: at the beginning of the study.
Day 8: after first treatment period.
Day 15: after washout period.
Day 22: after second treatment period.

In all cases the products were applied rectally as a fluid gel with an applicator dosing 5 ml. Patients applied 5 ml before going to bed every night during the whole week.

5.4.—Results and Conclusions

In the study there were two groups but at the time of expressing results, the groups were not taken into account. The results of the 20 patients are shown in Table 14 and 15.

Rectal Discomfort/Pain

The average results obtained after using the invention or the placebo compositions are shown in Table 14.

TABLE 14

|  | COMPOSITION | |
| --- | --- | --- |
|  | INVENTION | PLACEBO |
| Average ± s.d. | 29.7 | 53.55 |
| p | <0.000 | |

Rectal Tenesmus

The average results obtained after using the invention or placebo compositions are shown in Table 15:

TABLE 15

|  | COMPOSITION | |
| --- | --- | --- |
|  | INVENTION | PLACEBO |
| Average | 43.44 | 55.77 |
| p | 0.003 | |

As shown in Tables 14 and 15, the composition according to the invention, significantly reduces rectal discomfort/pain ($p<0.000$) and rectal tenesmus ($p=0.003$) in comparison with the placebo composition, in a group of 20 men when applied rectally once a day for a week.

Example 6.—Comparative Study of Treatment of Proctitis 6.1.—Objective, Subjects and Formulations The objective of the study was to compare the clinical efficacy of a composition comprising including xylitol, olive oil and TMG as active ingredients, with a composition comprising only olive oil as active ingredient, in patients with proctitis after prostate cancer treatment.

For the purpose of the study 9 patients were accepted into the study. Patients were randomly divided into 2 groups (one group with 4 patients and another one with 5 patients). Two different compositions were tested.

Composition A (invention), comprising 0.5% Olive oil, 4.0% TMG and 10% Xylitol.

Composition B (olive oil), comprising 0.5% Olive oil, without TMG and Xylitol.

6.2.—Inclusion and Exclusion Criteria

Inclusion Criteria

Patients diagnosed with proctitis due to oncological treatment suffering rectal discomfort/pain and rectal tenesmus were included in the study.

Exclusion Criteria

Those patients who did not comply with the inclusion criteria were excluded from the study.

6.3.—Study Design

The study design was such that everyman used both compositions randomly assigned and used both compositions subsequently in a crossover design with a washout period of 7 days between one and the other.

Products were packaged in white tubes identified with the number of patient. Content was kept in a closed envelope and only opened for data treatment.

Every complaint was assessed by a VAS (Visual analogue scale) 100 mm long.

VAS values resulted from rectal discomfort/pain and rectal tenesmus were obtained for every patient at four different days:

Day 0: at the beginning of the study.
Day 8: after first treatment period.
Day 15: after washout period.
Day 22: after second treatment period.

In all cases the product was applied rectally as a fluid gel with an applicator dosing 5 ml. Patients applied 5 ml before going to bed every night during the whole week.

6.4.—Results and Conclusions

In the study there were two groups but at the time of expressing results, the groups were not taken into account.

Rectal Discomfort/Pain

The average results after using the invention or olive oil compositions are shown in Table 16:

TABLE 16

|  | INVENTION | OLIVE OIL |
| --- | --- | --- |
| Average | 32.44 | 65.55 |
| p | <0.000 | |

Rectal Tenesmus

The average results obtained after using the invention or olive oil compositions are shown in Table 17:

TABLE 17

|  | INVENTION | OLIVE OIL |
| --- | --- | --- |
| Average | 37.44 | 62.11 |
| p | <0.000 | |

As shown in Tables 16 and 17, the composition of the invention, significantly reduces rectal discomfort/pain ($p<0.000$) and rectal tenesmus ($p<0.000$) in comparison with the composition comprising only 0.5% Olive oil as active ingredient, in a group of 9 men when applied rectally once a day for a week.

What is claimed is:

1. A method of treating Oncologic Treatment Induced Orogastrointestinal Mucositis in a human in need thereof consisting essentially of administering a therapeutically effective amount of a composition consisting essentially of olive oil, trimethylglycine, and xylitol to effectively treat the Oncologic Treatment Induced Orogastrointestinal Mucositis in the human in need thereof.

2. The method according to claim 1, wherein the olive oil is present in the composition at 0.1%-5% by weight.

3. The method according to claim 1, wherein the trimethylglycine is present in the composition at 0.1%-10% by weight.

4. The method according to claim 1, wherein the xylitol is present in the composition at 1%-50% by weight.

5. The method according to claim 1, wherein the composition further consists essentially of an antioxidant selected from the group consisting of hydroxytyrosol, tyrosol, oleuropein, and mixtures thereof.

6. The method according to claim 1, wherein the composition is a liquid.

7. The method according to claim 1, wherein the Oncologic Treatment Induced Orogastrointestinal Mucositis affects the oral cavity, tongue, lips, pharynx, esophagus, stomach, intestine, rectum, anus, nose, nasal tract, paranasal sinuses, throat, vocal cords, larynx, and combinations thereof of the human in need thereof.

8. The method according to claim 1, wherein the olive oil is present at 0.1%-5% by weight, the trimethylglycine is present at 0.1%-10% by weight and the xylitol is present at 1%-50% by weight.

* * * * *